US005832916A

United States Patent [19]

Lundberg

[11] Patent Number: 5,832,916

[45] Date of Patent: Nov. 10, 1998

[54] METHOD AND SYSTEM FOR CHECKING THE OPERABILITY OF ELECTRICAL-BASED COMPONENTS IN A BREATHING EQUIPMENT

[75] Inventor: Mats Lundberg, Bromma, Sweden

[73] Assignee: Interspiro AB, Liningö, Sweden

[21] Appl. No.: 604,073

[22] Filed: Feb. 20, 1996

[51] Int. Cl.[6] .......... A61M 16/00; A62B 9/00; A62B 27/00; G08B 3/00

[52] U.S. Cl. .......... 128/202.22; 128/204.21; 128/204.23; 128/204.18; 128/204.26; 128/205.23; 128/201.27; 128/201.28

[58] Field of Search .......... 128/204.21–23, 128/204.18, 204.26, 205.11, 205.22, 205.23, 202.22, 201.27, 201.28

[56] References Cited

U.S. PATENT DOCUMENTS

| | | | |
|---|---|---|---|
| 2,484,217 | 10/1949 | Gardenier | 128/202.22 |
| 3,224,409 | 12/1965 | Fenger et al. | 128/202.22 |
| 3,478,740 | 11/1969 | Wennberg | 128/202.22 |
| 3,870,012 | 3/1975 | Metivier | 128/202.22 |
| 3,957,044 | 5/1976 | Fletcher et al. | 128/202.22 |
| 4,796,467 | 1/1989 | Burt et al. . | |
| 4,846,166 | 7/1989 | Willeke | 128/202.22 |
| 5,033,818 | 7/1991 | Barr | 128/202.22 |
| 5,097,826 | 3/1992 | Gray et al. . | |
| 5,157,378 | 10/1992 | Stumberg et al. . | |
| 5,313,937 | 5/1994 | Zdrojkowski | 128/202.22 |
| 5,392,771 | 2/1995 | MOck et al. | 128/202.22 |
| 5,438,320 | 8/1995 | Taylor | 128/202.22 |
| 5,485,850 | 1/1996 | Dietz | 128/204.23 |
| 5,492,110 | 2/1996 | Lenz et al. | 128/204.23 |
| 5,503,145 | 4/1996 | Clough | 128/202.22 |

*Primary Examiner*—Mickey Yu
*Assistant Examiner*—Dinh X. Nguyen
*Attorney, Agent, or Firm*—Pollock, Vande Sande & Priddy

[57] ABSTRACT

A method of verifying and indicating proper or improper functioning of breathing apparatus for an irrespirable environment. The breathing apparatus includes gas supply for supplying a user with breathable gas, at least one electrical component, a processor connected to the at least one electrical component, and at least one status indicator connected to the processor. A test signal is generated with the processor. The test signal is sent to the at least one electronic component of the breathing apparatus. A response to the test signal is generated with the at least one electrical component of the breathing apparatus. The response is transmitted to the processor. The response is compared to a predetermined response corresponding to proper functioning of the at least one electronic component of the breathing apparatus with the processor to determine a status of the at least one electrical component of the breathing apparatus. An output signal is generated with the processor corresponding to the proper or improper functioning of the at least one electrical component of the breathing apparatus. The output signal is transmitted to the status indicator. A status signal is generated with the status indicator to indicate the proper or improper functioning of the at least one electrical component of the breathing apparatus.

20 Claims, 1 Drawing Sheet

METHOD AND SYSTEM FOR CHECKING THE OPERABILITY OF ELECTRICAL-BASED COMPONENTS IN A BREATHING EQUIPMENT

FIELD OF THE INVENTION

The present invention relates to a breathing equipment used, for example, by a diver, a firefighter, or personnel handling a hazardous material. In particular, the invention relates to a method and system for checking whether electrical, electronic, electro-mechanical, or opto-electronic components, including current or light conducting conduits in a wired embodiment of the present invention, are properly operating in the breathing equipment, and indicating a failure warning if any component malfunctions.

BACKGROUND OF THE INVENTION

The breathing equipment, such as a Self-Contained Breathing Apparatus (SCBA), is typically worn by a diver, a firefighter, or someone handling hazardous material prior to entering a non-breathable environment. Due to a significant increase in semiconductor layout density and the attendant miniaturization of many devices, electrical and electronic-based components have been used extensively in such breathing equipment, as described in several U.S. patents.

For example, U.S. Pat. No. 5,097,826 to Gray, et al. is directed to a pressure monitoring device for a self-contained breathing apparatus for monitoring pressure levels in the tank. The device includes, among other things, such electrical-based components as an electrical transducer, signal comparators, light emitting diodes, a voltage divider, a relaxation oscillator, a liquid interface, and a differential input amplifier.

Another example is U.S. Pat. No. 5,157,378 to Stumberg, et al. which discloses a monitoring and alarm system in conjunction with a firefighter's breathing equipment. Some of the electrical-based components in that system include a temperature sensor and a motion detector, such as a mercury or piezoelectric switch, for monitoring ambient temperature and motion of the firefighter, respectively. These components, as well as a piezoelectric buzzer for activating an audible alarm, are connected to a microprocessor.

As a result of this widespread use of electrical-based devices in the breathing equipment, it is very important to test them during its production. However, it is absolutely critical to check that electrical, electronic, electro-mechanical, or opto-electronic components, including current or light conducting conduits used in a breathing equipment are fully serviceable and faultless after the breathing equipment leaves a production facility. The electrical-based components may be damaged during the shipment or, more likely, after the breathing equipment has been used, for example, by a firefighter in a hazardous, high temperature situation. Thus, a user may need to perform an operational check of the electrical-based components in a breathing equipment after the actual use. Alternatively, the user may need to conduct an operational check before entering the non-breathable environment to ensure that the electrical-based components have not been damaged by prior use, or that their characteristics have not been altered. This is particularly true if the breathing equipment has not been used on a regular basis or for a prolonged period of time.

Thus, an urgent need exists for a method and system for checking the operability of electrical, electronic, electro-mechanical, or opto-electronic components and indicating a failure warning if any such component either fails or does not function according to predetermined specifications.

SUMMARY OF THE INVENTION

It is therefore an object of the invention to provide means for checking the operability of electrical-based components in a breathing equipment.

It is another object of the invention to provide a failure warning indication if at least one electrical-based component malfunctions.

It is yet another object of the invention to automatically initiate a check of the operation of all electrical-based components quickly and without requiring any action by the user.

These and other objects, features and advantages are accomplished by a system for checking the proper operability of at least one electrical-based component in a breathing equipment. Typically, the breathing equipment includes a high pressure gas container with a valve at its outlet opening, a breathing mask connected with the high pressure gas container via a pressure-reducing regulator, and some electrical-based components. In accordance with the present invention, the system comprises indicating means and processing means. The processing means are communicatively coupled with at least one electrical-based component and the indicating means. When the breathing equipment is activated upon opening of the valve, the processing means receive a status signal from at least one electrical-based component. If the status signal is not received, the indicating means are controlled by the processing means to provide the visual warning indication that at least one electrical-based component is not functioning properly.

In one embodiment of the present invention, the indicating means are enabled to provide the visual warning indication that at least one electrical-based component is not functioning properly.

In another embodiment of the present invention, the indicating means are disabled or blinked, i.e., turned on and off momentarily, to provide the visual warning indication that at least one electrical-based component is not functioning properly.

BRIEF DESCRIPTION OF THE DRAWINGS

The invention described above, as well as additional embodiments, aspects and features of the present invention will become evident and more clearly understood when considered in conjunction with the accompanying drawing which shows a block diagram of a system for checking the operability of at least one electrical-based component in a breathing equipment in accordance with one embodiment of the present invention.

DESCRIPTION OF THE PREFERRED EMBODIMENTS

Figure 1:
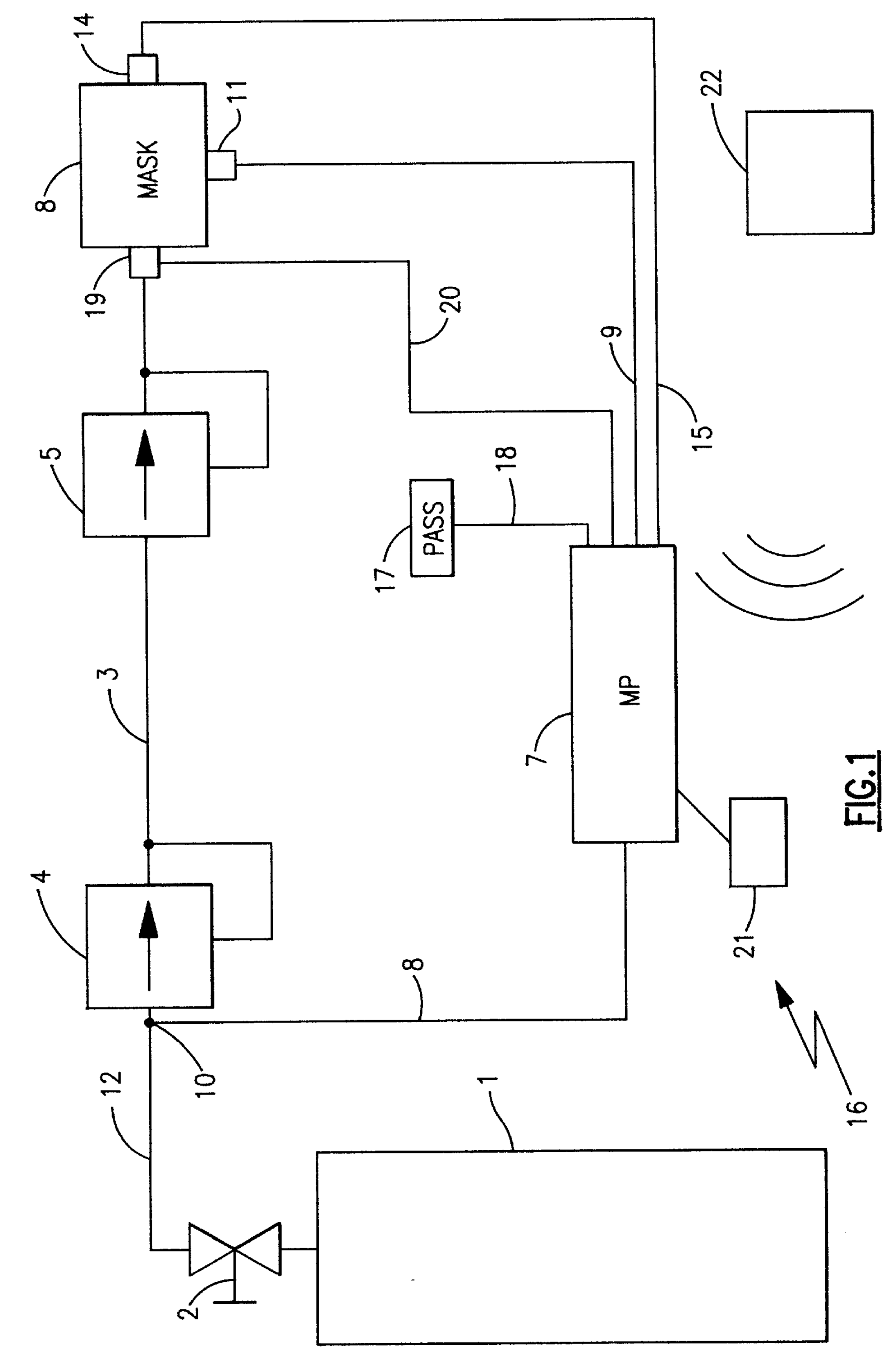

In accordance with the drawing, a breathing equipment 16 includes a gas reservoir, which is usually a gas cylinder or a gas container 1 containing breathing gas. The breathing gas may include, for instance, air or an oxygen-containing gas that typically includes at least 20 percent by volume oxygen and an inert gas, such as, for example, nitrogen or helium, at a pressure of normally 300 bars when the container is completely full. The gas container 1 includes an outlet opening in which a valve 2 is mounted. The gas container 1 is connected to a primary pressure regulator 4 through the valve 2. A line 3 extends from the primary pressure regulator 4 to a secondary pressure regulator 5 which is located immediately upstream of a breathing mask 6.

The primary pressure regulator 4 is adjusted to reduce the pressure in the gas container 1 to typically about 7 bars in the line 3 downstream of the primary pressure regulator 4. The secondary pressure regulator 5 still further reduces the pressure of the gas passing to the breathing mask 6, to a pressure of about 25 mm water column, that is, to a pressure suitable for use in the mask 6. As the wearer breathes, the pressure in the mask will oscillate around this value during a breathing phase, thereby constantly maintaining higher pressure. The secondary pressure regulator 5 is normally a requirement-controlled regulator which is closed prior to putting on the mask 6 and opened by the reduction in pressure that occurs when the wearer first inhales. The secondary pressure regulator 5 is opened when the relative pressure in the mask 6 falls below a predetermined value.

The drawing further shows a pressure sensor 10 responsive to the pressure at location 12, i.e., between the valve 2 and the primary pressure regulator 4. The pressure sensor 10 measures the pressure in the location 12 and is connected to a microprocessor 7 via a line 8. A line 9 extends from the microprocessor 7 to an indicator 11. In this embodiment, the indicator 11 is mounted in the breathing mask 6 and includes at least one indicating device, such as a light-emitting diode (LED) or other optical device. Preferably, at least one indicating device is provided for each function to be checked in the operational test. The indicator 11 provided in the breathing mask 6 is preferably visible to a user, both when the mask 6 is worn and when removed, and is also visible to others in the vicinity of the user.

A gas conduit, which connects the secondary pressure regulator 5 and the mask 6, contains a low-pressure sensor 19 which monitors the gas pressure after it has been reduced by the secondary pressure regulator 5. The low pressure sensor 19 is connected to the microprocessor 7 via a line 20.

The breathing mask 6 is preferably also provided with a differential pressure meter 14 connected to the microprocessor 7 via a line 15. The measured differential pressure is indicated by the indicator 11 which is visible to either a user wearing the mask 6 or to someone in the vicinity of the user.

The microprocessor 7, which may be a more complex computer system, is connected to a Personal Alert Safety System (PASS) unit 17 via a line 18. When activated, the PASS unit 17 indicates movement of the user wearing the breathing equipment 16. If the PASS unit 17 does not sense any movement by the user during a predetermined time interval, it will provide a warning signal to indicate that the user is motionless and may be in distress.

The lines 8, 9, 15, 18, and 20 may not be necessary as the microprocessor 7 may use wireless communication, as known in the art, to communicate with the pressure sensor 10, the indicator 11, the differential pressure meter 14, the PASS unit 17, and the low pressure sensor 19, respectively.

To check the operation of electrical-based components in the breathing equipment 16, the valve 2 is opened to initiate a gas pressure and start a gas flow from the high pressure gas container 1. This activates the breathing equipment 16 and the microprocessor 7, as well as the other electrical-based components, such as, the pressure sensor 10, the indicator 11, the differential pressure meter 14, the PASS unit 17, and the low-pressure sensor 19. As soon as the power-up occurs, each of the above electrical-based components sends a signal to the microprocessor 7 via its respective line. This signal indicates that the corresponding electrical-based component has been turned on and is functioning properly. This signal also confirms that there is no break in the current-carrying conduits, such as the lines 8, 9, 15, 18 and 20, which connect the pressure sensor 10, the indicator 11, the differential pressure meter 14, the PASS unit 17, and the low pressure sensor 19, respectively, to the microprocessor 7.

As soon as the microprocessor 7 receives the signal confirming that the electrical-based components are functioning properly, it sends a signal to the indicator 11. The indicator 11 preferably turns on the individual LEDs to provide a visual indication that all of the electrical-based components are functioning properly. As stated earlier, preferably each LED corresponds to the operational state of one electrical-based component.

If the microprocessor 7 does not receive a signal from the electrical-based component, then the indicator 11 is disabled, i.e., not turned on. Alternatively, the indicator 11 may be briefly turned on and then off, i.e., blinked, if the signal is not received. For example, if the pressure sensor 10 does not send the signal to the microprocessor 7 immediately after the power-up, then the microprocessor 7 disables, i.e., does not turn on or blinks the indicator 11. This notifies the user that a malfunction has occurred in at least one electrical-based component or a current-carrying conduit.

Alternatively, in another embodiment of the present invention, if the microprocessor 7 does not receive a signal confirming that an electrical-based component is functioning properly, then the indicator 11 is enabled. This provides a visual warning indication that at least one electrical-based component or the current-carrying conduit is not functioning properly.

In another embodiment of the present invention, after the power-up, the microprocessor 7 sends a test signal to each of the electrical-based components after the activation of the breathing equipment 16. After the test signal is individually received, for example, by the pressure sensor 10, the indicator 11, the differential pressure meter 14, the PASS unit 17, and the low pressure sensor 19, a status signal is sent from each of these electrical-based components to the microprocessor 7. The indicator 11, or preferably one LED, is disabled, i.e., not turned on or blinked, if the status signal is not received from any one of the electrical-based components. This provides a visual warning indication that at least one electrical-based component is not functioning properly. Alternatively, the indicator 11, or preferably one LED, may be turned on, if the status signal is not received from at least one of the electrical-based components to visually indicate that at least one electrical-based component is not functioning properly.

On the other hand, if the microprocessor 7 receives the status signal, it is then converted to a digital representation. The digital representation of the status signal is compared with a predetermined stored threshold representation corresponding to the proper operation of the electrical-based component. The indicator 11, or preferably one LED, is then disabled, i.e., blinked or not turned on, if the digital representation of the status signal differs from the predetermined stored threshold representation. Alternatively, the indicator 11, or preferably one LED, may be enabled, i.e., turned on, if the digital representation of the status signal differs from the predetermined stored threshold representation. Both options provide a visual warning indication that at least one electrical-based component is not functioning properly.

Another aspect of the present invention includes an LED in the indicator 11 which indicates whether the microprocessor 7 is malfunctioning. The LED, corresponding to the operating state of the microprocessor 7 in the indicator 11, would be turned on if the microprocessor 7 failed. Alternatively, in this embodiment, the LED may be disabled or blinked, as explained above, if the microprocessor 7 fails.

The present invention may also include a transmitter 21 attached to the breathing equipment 16. The transmitter 21 is controlled to send at least one signal to a receiver at a remotely located control station 22. The signal notifies the control station 22 of the status of the operational state of electrical-based components in the breathing equipment 16, that is, whether the electrical-based components are functioning properly, after they have been checked in accordance with the above description of the present invention.

It is understood, of course, that the breathing equipment 16 may include other electrical, electronic, electromechanical, or opto-electronic components in addition to those mentioned in the exemplary embodiments described above. It is also understood that the predetermined stored threshold representation may be a single value or a range of values between at least two values.

Since those skilled in the art can modify the disclosed specific embodiment without departing from the spirit of the invention, it is, therefore, intended that the claims be interpreted to cover such modifications and equivalents.

What is claimed is:

1. A method of verifying and indicating proper or improper functioning of breathing apparatus for an irrespirable environment, the breathing apparatus comprising means for supplying a user with breathable gas, at least one electrical component, a processor connected to the at least one electrical component, and at least one status indicator connected to the processor, said method comprising the steps of:

generating a test signal with the processor;

sending the test signal to the at least one electronic component of the breathing apparatus;

generating a response to the test signal with the at least one electrical component of the breathing apparatus;

transmitting the response to the processor;

comparing the response to a predetermined response corresponding to proper functioning of the at least one electronic component of the breathing apparatus with the processor to determine a status of the at least one electrical component of the breathing apparatus;

generating an output signal with the processor corresponding to the proper or improper functioning of the at least one electrical component of the breathing apparatus;

transmitting said output signal to the status indicator; and generating a status signal with the status indicator to indicate the proper or improper functioning of the at least one electrical component of the breathing apparatus.

2. The method according to claim 1, wherein a status signal indicating improper functioning of the at least one component of the breathing apparatus is generated upon failure to perform at least one of the steps of:

generating a test signal with the processor, sending the test signal to the at least one electronic component of the breathing apparatus;

generating a response to the test signal with the at least one electrical component of the breathing apparatus;

transmitting the response to the processor;

comparing the response to a predetermined response corresponding to proper functioning of the at least one electronic component of the breathing apparatus with the processor to determine a status of the at least one electrical component of the breathing apparatus;

generating an output signal with the processor corresponding to the proper or improper functioning of the at least one electrical component of the breathing apparatus; and transmitting said output signal to the status indicator.

3. The method according to claim 1, wherein said method is initiated upon activation of the at least one electrical component of the breathing apparatus.

4. The method according to claim 1, wherein said method is performed whenever said at least one electrical component is activated.

5. The method according to claim 1, wherein said method is performed after activation of the at least one electrical component of the breathing apparatus.

6. The method according to claim 1, wherein said status signal generated with the status indicator is visible.

7. The method according to claim 1, wherein said status signal generated with the status indicator is audible.

8. The method according to claim 1, wherein said output signal is transmitted to a remotely located control station.

9. The method according to claim 1, wherein the indicator may be activated or inactivated to indicate the status of the at least one electrical component.

10. The method according to claim 1, wherein the processor generates the test signal in response to supplying of breathable gas to the breathing apparatus.

11. A method of verifying and indicating proper or improper functioning of breathing apparatus for an irrespirable environment, the breathing apparatus comprising means for supplying a user with breathable gas, at least one electrical component, a processor connected to the at least one electrical component, and at least one status indicator connected to the processor, said method comprising the steps of:

receiving with the processor a status signal corresponding to a status of the at least one electrical component;

comparing the status to a predetermined response corresponding to proper functioning of the at least one electronic component of the breathing apparatus with the processor to determine a status of the at least one electrical component of the breathing apparatus;

generating an output signal with the processor corresponding to the proper or improper functioning of the at least one electrical component of the breathing apparatus;

transmitting said output signal to the status indicator; and generating a status signal with the status indicator to indicate the proper or improper functioning of the at least one electrical component of the breathing apparatus.

12. The method according to claim 11, wherein said status signal is generated by the at least one electrical apparatus in response to a test signal generated by the processor and sent to the at least one electronic component of the breathing apparatus.

13. The method according to claim 11, wherein the status signal includes a lack of signal from said at least one electrical component.

14. A system for verifying and indicating proper or improper functioning of breathing apparatus for an irrespirable environment that includes at least one electrical component, said system comprising:

a processor communicatively coupled with the at least one electrical component for generating a test signal, transmitting the test signal to the at least one electrical component, receiving a response to the test signal from the at least one electrical component, comparing the response to a predetermined response to determine status of the at least one electrical component, generating an output signal corresponding to the status of the at least one electrical component; and a status indicator communicatively coupled with the processor for receiving the output signal from the processor and generating a status signal indicating the proper or improper functioning of the at least one electrical component.

15. The system according to claim 14, further comprising:

a transmitter communicatively coupled with the processor; and a receiver communicatively coupled with the transmitter.

16. The system according to claim 14, wherein the indicator is visual.

17. The system according to claim 14, wherein the indicator is audible.

18. The system according to claim 14, wherein said predetermined response is a single value.

19. The system according to claim 14, wherein said predetermined response is a range of values between at least two values.

20. A system for verifying and indicating proper or improper functioning of breathing apparatus for an irrespirable environment that includes at least one electrical component, said system comprising:

a processor communicatively coupled with the at least one electrical component for receiving a status signal from the at least one electrical component, comparing the status signal to a predetermined response to determine status of the at least one electrical component, generating an output signal corresponding to the status of the at least one electrical component; and a status indicator communicatively coupled with the processor for receiving the output signal from the processor and generating a status signal indicating the proper or improper functioning of the at least one electrical component.

* * * * *

UNITED STATES PATENT AND TRADEMARK OFFICE

CERTIFICATE OF CORRECTION

PATENT NO. : 5,832,916
DATED : November 10, 1998
INVENTOR(S) : Mats Lundberg

It is certified that error appears in the above-identified patent and that said Letters Patent is hereby corrected as shown below:

On the title page,Item [73],

The Assignee's city of residence is --Lidingö--, not "Liningö".

Signed and Sealed this

Fourth Day of May, 1999

*Attest:*

Q. TODD DICKINSON

*Attesting Officer*

*Acting Commissioner of Patents and Trademarks*